US006252111B1

(12) United States Patent
Sakai et al.

(10) Patent No.: US 6,252,111 B1
(45) Date of Patent: Jun. 26, 2001

(54) METHOD FOR PRODUCING SULFONIMIDE OR ITS SALT

(75) Inventors: Shigenori Sakai, Yamaguchi; Hironari Takase, Saitama; Hiroaki Sakaguchi, Yamaguchi, all of (JP)

(73) Assignee: Central Glass Company, Limited, Ube (JP)

(*) Notice: Subject to any disclaimer, the term of this patent is extended or adjusted under 35 U.S.C. 154(b) by 0 days.

(21) Appl. No.: 09/504,113

(22) Filed: Feb. 15, 2000

(30) Foreign Application Priority Data

Feb. 16, 1999 (JP) .................................. 11-036631

(51) Int. Cl.⁷ ..................... C07C 303/34; C07C 303/44
(52) U.S. Cl. .................................. 564/82; 564/96
(58) Field of Search ........................... 564/96, 82

(56) References Cited

U.S. PATENT DOCUMENTS

| 4,600,758 | * | 7/1986 | Dolak et al. | 546/200 |
| 5,723,664 | | 3/1998 | Sakaguchi | 564/32 |

FOREIGN PATENT DOCUMENTS

| 2 763 331 | 11/1998 | (FR) . |
| 8-81436 | 3/1996 | (JP) . |
| WO 90/11999 | 10/1990 | (WO) . |
| WO 97/23448 | 7/1997 | (WO) . |

* cited by examiner

Primary Examiner—Peter O'Sullivan
(74) Attorney, Agent, or Firm—Crowell & Moring, L.L.P.

(57) ABSTRACT

The invention relates to a method for producing a sulfonimide or its alkali metal salt. The method includes the steps of (a) reacting a precursory salt of the sulfonimide with a base contained in a basic aqueous solution, thereby producing a first aqueous solution containing the alkali metal salt and an amine; (b) removing the amine from the first aqueous solution to obtain a second aqueous solution containing the alkali metal salt; and (c) crystallizing the alkali metal salt in the second aqueous solution. The base is potassium hydroxide, sodium hydroxide or lithium hydroxide. The base is added to the second aqueous solution to generate the crystallization. The precursory salt is formed when the sulfonimide is reacted with a tertiary amine or a heterocyclic amine. The alkali metal salt is produced easily and economically in an industrial scale production with high purity and high yield.

18 Claims, No Drawings

METHOD FOR PRODUCING SULFONIMIDE OR ITS SALT

BACKGROUND OF THE INVENTION

The present invention relates to a method for producing a sulfonimide or its salt. Sulfonimide compounds are useful as Lewis acid catalysts and ion transport agents, in the fields of organic compound syntheses, electrolytes and the like.

U.S. Pat. No. 5,723,664, corresponding to Japanese Patent Publication JP-A-8-81436, discloses a method for producing a sulfonimide or its salt. The product obtained by this method, however, may contain an impurity such as (1) a sulfonamide represented by the general formula $RfSO_2NH_2$ or (2) a sulfonic acid represented by the general formula $RfSO_3H$. The removal of this impurity may prevent a problem of the decrease of potential of an aluminum collector and other problems, when the product (i.e., lithium salt of sulfonimide) is used for electrolyte of a lithium cell.

SUMMARY OF THE INVENTION

It is therefore an object of the present invention to provide a method for producing a sulfonimnide or its salt with high purity, which method is economical in an industrial scale production.

According to the present invention, there is provided a method for producing a sulfonimide represented by the general formula (1), an alkali metal salt thereof represented by the general formula (2), or another salt thereof represented by the general formula (3).

$$H[Rf^1SO_2-N-SO_2Rf^2] \quad (1)$$

where $Rf^1$ and $Rf^2$ represent the same or different groups each of which has a carbon atom number from 1 to 12 and is straight-chain or branched-chain and one selected from the group consisting of perfluoroalkyl groups, fluoroalkyl groups, fluoroalkenyl groups and fluoroallyl groups, $$A[Rf^1SO_2-N-SO_2Rf^2] \quad (2)$$

where A is an alkali metal selected from the group consisting of K, Na and Li, and $Rf^1$ and $Rf^2$ are defined as above, $$M^1[Rf^1SO_2-N-SO_2Rf^2]_{n1} \quad (3)$$

where $M^1$ represents a positive ion having a first valence, $Rf^1$ and $Rf^2$ are defined as above, and n1 represents an integer that is the same as said first valence. This method comprises (a) reacting a precursor salt of said sulfonimnide with a base contained in a basic aqueous solution, said base being selected from the group consisting of potassium hydroxide, sodium hydroxide and lithium hydroxide, said precursory salt being represented by the general formula (4) and formed when said sulfonimide is reacted with a tertiary amine or a heterocyclic amine, said tertiary amine being represented by the general formula (5), thereby producing a first aqueous solution comprising said alkali metal salt and an amine; (b) removing said amine from said first aqueous solution to obtain a second aqueous solution comprising said alkali metal salt; and (c) crystallizing said alkali metal salt in said second aqueous solution, $$M^2[Rf^1SO_2-N-SO_2Rf^2]_{n2} \quad (4)$$

where $M^2$ represents a positive ion having a second valence, $Rf^1$ and $Rf^2$ are defined as above, and n2 represents an integer that is the same as said second valence, $$(R^1)_3N \quad (5)$$

where $R^1$ represents the same ox different alkyl groups each having a carbon atom number of from 1 to 5.

According to the invention, it becomes possible to obtain the alkali metal salt with high purity by crystallizing the alkali metal salt in the second aqueous solution.

In the invention, the method further optionally comprises reacting said alkali metal salt, which has been obtained by the crystallizing, with a strong acid, thereby producing the sulfonimide. The method still further optionally comprises reacting the sulfonimide with a compound selected from the group consisting of metal hydroxides, metal oxides, metal carbonates, metal acetates, ammonia and substituted ammonias, thereby producing said another salt of said sulfonimide with high purity.

DESCRIPTION OF THE PREFERRED EMBODIMENTS

It is possible to conduct the crystallization of the alkali metal salt in the second aqueous solution by adjusting the concentration of a base (e.g., potassium hydroxide), which is the same as that used in the reaction with the precursory salt of the sulfonimide, in the second aqueous solution. This adjustment can be conducted by adding the base to the second aqueous solution to increase the concentration.

Prior to the reaction of the precursor salt of the sulfonimnide with the base, it is optional to conduct the following exemplary reactions, as follows. At first, one or two sulfonyl fluorides or chlorides, which are represented by the formulas $Rf^1SO_2NH_2$ and $Rf^2SO_2X$, are reacted with a tertiary amine, which is represented by the formula $(R^1)_3N$, as expressed by the following reaction formula.

$$Rf^1SO_2NH_2+Rf^2SO_2X+2(R^1)_3N \rightarrow (R^1)_3NH^+(Rf^1SO_2NSO_2Rf^2)^- + (R^1)_3NH^+X^-$$

where $Rf^1$, $Rf^2$ and $R^1$ are defined as above, and X is fluorine or chlorine. This reaction is disclosed in U.S. Pat. No. 5,723,664, of which disclosure is incorporated herein by reference. Then, the obtained precursor salt of the sulfonimide, which is represented by the formula $(R^1)_3NH^{+(Rf1}SO_2-N-SO_2Rf^2)^-$, is reacted with the base, which is represented by AOH, by adding the base to the reaction product, as expressed by the following reaction formula.

$$(R^1)_3NH^{+(Rf1}SO_2NSO_2Rf^2)^- + (R^1)_3NH^+X^- + 2AOH \rightarrow A^+(Rf^1SO_2NSO_2Rf^2)^- + 2(R^1)_3N + A^+X^{31} + 2H_2O$$

where A is defined as above. Then, a by-product, which is represented by the formula AX and insoluble, is removed from the reaction product (first aqueous solution) by filtration. After that, another by-product, that is, tertiary amine represented by the formula $(R^1)_3N$, is distilled away, thereby obtaining the second aqueous solution. Then, the base, which is the same as that used in the reaction with the precursory salt, is added to the second aqueous solution such that the alkali metal salt, which is represented by the formula $A[Rf^1SO_2-N-SO_2Rf^2]$, is crystallized in the remaining aqueous solution. With this crystallization, the alkali metal salt is separated from an impurity dissolved in the remaining aqueous solution. Therefore, it becomes possible to obtain the alkali metal salt with high purity by filtration. This impurity may contain (1) a sulfonamide salt represented by the general formula RfSO$_2$NHA and/or (2) a sulfonate represented by the general formula RfSO$_3$A where Rf is identical with the abovedefined Rf$^1$ or Rf$^2$ and A is defined as above. The thus obtained alkali metal salt may be reacted with a strong acid (e.g., concentrated sulfric acid), followed by distillation, thereby obtaining the sulfonimide represented by the formula H[Rf$^1$SO$_2$—N—SO$_2$Rf$^2$]. Furthermore, this sulfonimide may be reacted with a compound selected from the group consisting of metal hydroxides, metal oxides, metal carbonates, metal acetates, ammonia and substituted ammonias, thereby producing the another salt of the sulfonimide with high purity, represented by the formula M$^1$[Rf$^1$SO$_2$—N—SO$_2$Rf$^2$]$_{n1}$.

In case that the base is potassium hydroxide, the reaction of the precursor salt with the base can be conducted at a temperature of 80–90° C. Within this range, it becomes possible to distill the tertiary amine (R$^1$)$_3$N away. If the reaction temperature is out of this range, the amine may be dissolved into the potassium hydroxide aqueous solution. With this, the degree of the crystallization of the alkali metal salt from the aqueous solution may become insufficient. The concentration of the potassium hydroxide in the potassium hydroxide aqueous solution is adjusted to preferably at least 1.5 moles, more preferably falling within a range of 1.5–3.6 moles, per liter of the potassium hydroxide aqueous solution. If it is less than 1.5 moles per liter, the degree of crystallization of the alkali metal salt (potassium sulfonimide) may become insufficient. If it is greater than 3.6 moles per liter, the above-mentioned impurities, that is, the sulfonamide salt and the sulfonate may precipitate in the potassium hydroxide aqueous solution. With this, the alkali metal salt may become inferior in purity. In case that the base is potassium hydroxide, the crystallization is conducted at a temperature preferably of 10–25° C., more preferably of about 20° C., in order to obtain potassium sulfonimide with high yield. Within this temperature range, the above-mentioned impurities are dissolved in the aqueous solution. Therefore, it becomes possible to obtain potassium sulfonimide with high purity by filtration.

In case that the base is sodium hydroxide or lithium hydroxide, the reaction of the precursor salt with the base can be conducted at a temperature of 50–70° C. If the reaction temperature is out of this range, the degree of the crystallization of the alkali metal salt from the aqueous solution may become insufficient, as in the case of potassium hydroxide. The concentration of the sodium hydroxide in the sodium hydroxide aqueous solution is adjusted to preferably at least 6.5 moles, more preferably falling within a range of 7.2–8.0 moles, per liter of the sodium hydroxide aqueous solution, in order to prevent the disadvantages mentioned in the case of potassium hydroxide. The concentration of the lithium hydroxide in the lithium hydroxide aqueous solution is adjusted to preferably at least 3.3 moles, more preferably falling within a range of 3.3–4.6 moles, per liter of the lithium hydroxide aqueous solution, in order to prevent the disadvantages mentioned in the case of potassium hydroxide. In case that the base is sodium hydroxide or lithium hydroxide, the crystallization is conducted at a temperature preferably of 15–30° C., more preferably of about 25° C., in order to obtain sodium sulfonimide or lithium sulfonimide with high yield.

The following examples are illustrative of the present invention, but these examples are not limitative.

EXAMPLE 1

At first, 8755 g of triethylamine was put into a stainless steel (SUS) autoclave. Then, this autoclave was charged with 720 g of anhydrous ammonia and 7070 g of trifluoromethanesulfonylfluoride [CF$_3$SO$_2$F], under cooling with ice. Then, the temperature of the autoclave was increased to room temperature (26° C.), thereby conducting the reaction for 18 hr. After the reaction, ammonium fluoride was removed from the reaction mixture by filtration. Then, a portion (400 g) of the obtained reaction mixture was put into a glass beaker. This portion contained 202 g of triethylammonium salt of bis((trifluoromethyl)sulfonyl) imide [(C$_2$H$_5$)$_3$NH$^+$(CF$_3$SO$_2$)$_2$N$^-$], 64 g of triethylammonium fluoride [(C$_2$H$_5$)$_3$NH$^+$F$^-$], 121 g of triethylamine, 9.6 g of trifluoromethylsulfonyl amide (impurity) CF$_3$SO$_2$NH$_2$, and 3.6 g of triethylammonium salt of trifluoromethanesulfonate [(C$_2$H$_5$)$_3$NH$^+$CF$_3$SO$_3^-$]. Then, a potassium hydroxide aqueous solution containing 313 g of KOH was added to the beaker, followed by mixing, thereby conducting the reaction at 80° C. After that, triethylamine produced by the reaction was distilled out of the KOH aqueous solution containing the reaction products. Then, the resultant KOH aqueous solution was adjusted to having a KOH concentration of 3.4 moles per liter of the solution by adding a KOH aqueous solution. Under this condition, potassium salt of bis((trifluoromethyl)sulfonyl) imide [K(CF$_3$SO$_2$)$_2$N] was allowed to crystallize at 25° C. in the solution, followed by filtration, thereby obtaining 161 g of this potassium salt. The yield was 95%. This potassium salt contained 0.7 g of trifluoromethanesulfoneamidepotassium [CF$_3$SO$_2$NHK] and 0.2 g of trifluoromethanesulfonic potassium [CF$_3$SO$_3$K] as impurities.

COMPARATIVE EXAMPLE 1

The procedures of Example 1 until putting a portion (400 g) of the obtained reaction mixture into a glass beaker were repeated in this comparative example. Then, a potassium hydroxide aqueous solution containing 60 g of KOH was added to the beaker, followed by mixing, thereby conducting the reaction at 80° C. After that, triethylamine and water were distilled out of the KOH aqueous solution containing the reaction products. Then, the remaining solution was evaporated to dryness at 120° C., thereby obtaining 164 g of potassium salt of bis((trifluoromethyl)sulfonyl) imide. The yield was 97%. This potassium salt contained 10.8 g of trifuoromethanesulfoneamidepotassium and 2.7 g of trifluoromethanesulfonic potassium as impurities.

EXAMPLE 2

At first, a flask was charged with 2000 g of acetonitrile and 1000 g of trifluoromethanesulfonylchloride [CF$_3$SO$_2$Cl]. Then, the flask was further charged with 101 g of anhydrous ammonia and 600 g of triethylamine, under cooling with ice. Then, the temperature of the flask was increased to room temperature (23° C.), thereby conducting the reaction for 5 hr. After the reaction, ammonium chloride was removed from the reaction mixture by filtration. Then, a portion (1250 g) of this reaction mixture was put into a glass beaker. This portion contained 352 g of triethylammonium salt of bis((triuoromethyl)sulfonyl) imide, 127 g of triethylammonium chloride (C$_2$H$_5$)$_3$NH$^+$Cl$^-$, 728 g of acetonitrile, 25.2 g of trifluoromethylsulfonyl amide (impurity), and 17.6 g of triethylammonium salt of trifluoromethanesulfonate. Then, a potassium hydroxide aqueous solution containing 418 g of KOH was added to the beaker, followed by mixing, thereby conducting the reaction at 80° C. After that, triethylamine and acetonitrile were distilled out of the KOH aqueous solution containing the reaction products. Then, the resultant KOH aqueous solution was adjusted to having a KOH concentration of 3.6 moles per liter of the solution by adding a KOH aqueous solution. Under this condition, potassium salt of bis((trinfuoromethyl) sulfonyl) imide was allowed to crystallize at 23° C. in the solution, followed by filtration, thereby obtaining 288 g of this potassium salt. The yield was 98%. This potassium salt contained 1.2 g of trifluoromethanesulfoneamidepotassium and 0.1 g of trifluoromethanesulfonic potassium as impurities.

COMPARATIVE EXAMPLE 2

The procedures of Example 2 until obtaining the reaction mixture were repeated. Then, a portion (1250 g) of this reaction mixture was put into a glass beaker. Then, a potassium hydroxide aqueous solution containing 103 g of KOH was added to the beaker, followed by mixing, thereby conducting the reaction at 80° C. After that, triethylamine, acetonitrile and water were distilled out of the KOH aqueous solution containing the reaction products. Then, the remaining solution was evaporated to dryness at 120° C., thereby obtaining 288 g of potassium salt of bis((trifluoromethyl) sulfonyl) imnide. The yield was 98%. This potassium salt contained 28.4 g of trifluoromethanesulfoneamidepotassium and 13.2 g of trifluoromethanesulfonic potassium as impurities.

EXAMPLE 3

At first, a flask was charged with 2550 g of acetonitrile, 1198 g of trifluoromethanesulfoneamide [$CF_3SO_2NH_2$], 2915 g of N-nonafluorobutanesulfonylfluoride [$C_4F_9SO_2F$] and 2437 g of triethylamine, thereby conducting the reaction for 5 hr at 70° C. Then, a portion (800 g) of the reaction mixture was put into a glass beaker. This portion contained 491 g of triethylammonium salt of trifluoromethanesulfonyl-N-nonafluorosulfonyl imide [$(C^2H_5)_3NH^+(CF_3SO_2)(C_4F_9SO_2)N^{-}$], 112 g of triethylammonium fluoride, 139 g of acetonitrile, 17.5 g of trifiuoromethylsulfonyl amide (impurity), 1.5 g of triethylammonium salt of trifluoromethanesulfonate and 39.3 g of N-nonafluorobutanesulfonyl amide. Then, a potassium hydroxide aqueous solution containing 323 g of KOH was added to the beaker, followed by mixing, thereby conducting the reaction at 80° C. After that, triethylamine and acetonitrile were distilled out of the KOH aqueous solution containing the reaction products. Then, the resultant KOH aqueous solution was adjusted to having a KOH concentration of 1.6 moles per liter of the solution by adding a KOH aqueous solution. Under this condition, potassium salt of trifluoromethanesulfonyl-N-nonafluorosulfonyl imide [$K(CF_3SO_2)(C_4F_9SO_2)N$] was allowed to crystallize at 22° C. in the solution, followed by filtration, thereby obtaining 411 g of this potassium salt. The yield was 95%. This potassium salt contained 5.6 g of trifluoromethanesulfoneaxnidepotassium, 0.1 g of trifluoromethanesulfonic potassium and 8.9 g of N-nonafluorobutanesulfonicamidepotassium as impurities.

COMPARATIVE EXAMPLE 3

The procedures of Example 3 until obtaining the reaction mixture were repeated. Then, a portion (800 g) of this reaction mixture was put into a glass beaker. Then, a potassium hydroxide aqueous solution containing 103 g of KOH was added to the beaker, followed by mixing, thereby conducting the reaction at 80° C. After that, triethylamine, acetonitrile and water were distilled out of the KOH aqueous solution containing the reaction products. Then, the remaining solution was evaporated to dryness at 120° C., thereby obtaining 420 g of potassium salt of trifiuoromethanesulfonyl-N-nonafluorosulfonyl imide. The yield was 97%. This potassium salt contained 22.7 g of trifluoxomethanesulfoneamidepotassium, 1.1 g of trifluoromethanesulfonic potassium and 44.3 g of N-nonafluorobutanesulfoneidepotassium [$C_4F_9SO_2NHK$] as impurities.

EXAMPLE 4

At first, 2706 g of triethylamine was put into a stainless steel (SUS) autoclave. Then, this autoclave was charged with 260 g of anhydrous ammonia and 2560 g of trifluoraethanesulfonylffuoride [$CF_3SO_2F$], under cooling with ice. Then, the temperature of the autoclave was increased to room temperature (28° C.), thereby conducting the reaction for 10 hr. After the reaction, ammonium fluoride was removed from the reaction mixture by filtration. Then, a portion (200 g) of the reaction mixture was put into a glass beaker. This portion contained 130 g of triethylammonium salt of bis((trifluoromethyl)sulfonyl) imide, 41 g of triethylammonium fluoride, 23 g of triethylamine, 3.9 g of trifluoromethylsulfonyl amide (impurity), and 2.2 g of triethylammoniunm salt of trifluoromethanesulfonate. Then, a sodium hydroxide aqueous solution containing 27 g of NaOH was added to the beaker, followed by mixing, thereby conducting the reaction at 60° C. After that, sodium fluoride produced by the reaction was removed by filtration from the NaOH aqueous solution containing reaction products. Then, triethylamine produced by the reaction was distilled out of the solution. Then, the resultant NaOH aqueous solution was adjusted to having a NaOU concentration of 7.6 moles per liter of the solution by adding 233 g of NaOH to the solution. Under this condition, sodium salt of bis((trifluoromethyl) sulfonyl) imide was allowed to crystallize at 25° C. in the solution, followed by filtration, thereby obtaining 44 g of this sodium salt. The yield was 43%. This sodium salt contained 0.8 g of trifluoromethanesulfoneamidesodium and 0.3 g of trifluoromethanesulfonic sodium as impurities.

COMPARATIVE EXAMPLE 4

The procedures of Example 4 until obtaining the reaction mixture were repeated. Then, a portion (200 g) of this reaction mixture was put into a glass beaker. Then, a sodium hydroxide aqueous solution containing 27 g of NaOH was added to the beaker, followed by mixing, thereby conducting the reaction at 60° C. After that, sodium fluoride was removed by filtration from the solution containing the reaction products. Then, triethylamine and water were distilled out of the solution. Then, the remaining solution was evaporated to dryness at 120° C., thereby obtaining 101 g of sodium salt of bis((trifluoromethyl)sulfonyl) imide. The yield was 98%. This sodium salt contained 4.6 g of trifluoromethanesulfoneamidesodium and 1.5 g of trifluoromethanesulfonic sodium as impurities.

EXAMPLE 5

The procedures of Example 4 until obtaining the reaction mixture were repeated. Then, a portion (200 g) of this reaction mixture was put into a glass beaker. Then, a lithium hydroxide aqueous solution containing 16 g of LiOH was added to the beaker, followed by mixing, thereby conducting the reaction at 60° C. After that, lithium fluoride produced by the reaction was removed by filtration from the LiOH aqueous solution containing reaction products. Then, triethylamine produced by the reaction was distilled out of the solution. Then, the resultant LiOH aqueous solution was adjusted to having a LiOH concentration of 4.6 moles per liter of the solution by adding 54 g of LiOH to the solution. Under this condition, lithium salt of bis((trifluoromethyl)sulfonyl) imide was allowed to crystallize at 25° C. in the solution, followed by filtration, thereby obtaining 20 g of this lithium salt. The yield was 20%. This lithium salt contained 0.5 g of trifluoromethanesulfoneamidelithium and 0.1 g of trifluoromethanesulfonic lithium as impurities.

COMPARATIVE EXAMPLE 5

The procedures of Example 5 until obtaining the reaction mixture were repeated. Then, a portion (200 g) of this reaction mixture was put into a glass beaker. Then, a lithium hydroxide aqueous solution containing 16 g of LiOH was added to the beaker, followed by mixing, thereby conducting the reaction at 60° C. After that, lithium fluoride produced by the reaction was removed by filtration from the LiOH aqueous solution containing reaction products. Then, triethylamine and water were distilled out of the solution at 80° C. Then, the remaining solution was evaporated to dryness at 120° C., thereby obtaining 96 g of lithium salt of bis((trifluoromethyl)sulfonyl) imide. The yield was 98%. This lithium salt contained 4.2 g of trifluoromethanesulfoneamidelithium and 1.4 g of trifluoromethanesulfonic lithium as impurities.

The entire disclosure of each of Japanese Patent Application Nos. 11-36631 filed on Feb. 16, 2000 and 2000-35458 filed on Feb. 14, 2000, including specification, claims, and summary, is incorporated herein by reference in its entirety.

What is claimed is:

1. A method for producing a sulfonimide represented by the general formula (1), an alkali metal salt thereof represented by the general formula (2), or another salt thereof represented by the general formula (3), said method comprising:

reacting a precursory salt of said sulfonimide with a base contained in a basic aqueous solution, said base being selected from the group consisting of potassium hydroxide, sodium hydroxide and lithium hydroxide, said precursory salt being represented by the general formula (4) and formed when said sulfonimide is reacted with a tertiary amine or a heterocyclic amine, said tertiary amine being represented by the general formula (5), thereby producing a first aqueous solution comprising said alkali metal said, an amine, and an impurity comprising at lease one of a sulfonamide salt represented by the general formula (6) or a sulfonate represented by the general formula (7);

removing said amine from said first aqueous solution to obtain a second aqueous solution comprising said alkali metal salt and said impurity; and crystallizing said alkali metal salt in said second aqueous solution by increasing a concentration of said base in said second agueous solution such that said alkali metal salt is separated from said impurity, $$H[Rf^1SO_2—N—SO_2Rf^2] \quad (1)$$

where $Rf^1$ and $Rf^2$ represent the same or different groups each of which has a carbon atom number from 1 to 12 and is straight-chain or branched-chain and one selected from the group consisting of perfluoroalkyl groups, fluoroalkyl groups, fluoroalkenyl groups and fluoroallyl groups, $$A[Rf^1SO_2—N—SO_2Rf^2] \quad (2)$$

where A is an alkali metal selected from the group consisting of K, Na and Li, and $Rf^1$ and $Rf^2$ are defined as above, $$M^1[Rf^1SO_2Rf^2]_{n1} \quad (3)$$

where $M^1$ represents a positive ion having a first valence, $Rf^1$ and $Rf^2$ are defined as above, and n1 represents an integer that is the same as said first valence, $$M^2[Rf^1SO_2—N—SO_2Rf^2]_{n2} \quad (4)$$

where $M^2$ represents a positive ion having a second valence, $Rf^1$ and $Rf^2$ are defined as above, and n2 represents an integer that is the same as said second valence, $$(R^1)_3N \quad (5)$$

where $R^1$ represents the same or different alkyl groups each having a carbon atom number of from 1 to 5

$$RfSO_2NHA \quad (6)$$

where Rf is identical with $Rf^1$ or $Rf^2$, and A is defined as above, $$RfSO_3A \quad (7)$$

where Rf and A are defined as above.

2. A method according to claim 1, wherein, after said removing, said base is added to said second aqueous solution such that said alkali metal salt is crystallized in said second aqueous solution.

3. A method according to claim 1, wherein said base is potassium hydroxide.

4. A method according to claim 3, wherein said reacting is conducted at a temperature of 80–90° C.

5. A method according to claim 3, wherein a concentration of said potassium hydroxide in said second aqueous solution is adjusted to at least 1.5 moles per liter of said second aqueous solution.

6. A method according to claim 5, wherein said concentration is adjusted to falling within a range of 1.5–3.6 moles per liter of said second aqueous solution.

7. A method according to claim 3, wherein said crystallizing is conducted at a temperature of 10–25° C.

8. A method according to claim 1, wherein, after said crystallizing, said alkali metal salt is obtained by filtration.

9. A method according to claim 1, wherein said base is selected from the group consisting of sodium hydroxide and lithium hydroxide.

10. A method according to claim 9, wherein said reacting is conducted at a temperature of 50–70° C.

11. A method according to claim 9, wherein said base is sodium hydroxide, and a concentration of said sodium hydroxide in said second aqueous solution is adjusted to at least 6.5 moles per liter of said second aqueous solution.

12. A method according to claim 11, wherein said concentration is adjusted to falling within a range of 7.2–8.0 moles per liter of said second aqueous solution.

13. A method according to claim 9, wherein said base is lithium hydroxide, and a concentration of said lithium hydroxide in said second aqueous solution is adjusted to at least 3.3 moles per liter of said second aqueous solution.

14. A method according to claim 13, wherein said concentration is adjusted to failing within a range of 3.3–4.6 moles per liter of said second aqueous solution.

15. A method according to claim 9, wherein said crystallizing is conducted at a temperature of 15–30° C.

16. A method according to claim 1, wherein said alkali metal salt obtained by said crystallizing is reacted with a strong acid, thereby producing said sulfonimide.

17. A method according to claim 16, wherein said strong acid is sulfuric acid.

18. A method according to claim 16, wherein said sulfonimide produced by said reacting is reacted with a compound selected from the group consisting of metal hydroxides, metal oxides, metal carbonates, metal acetates, ammonia and substituted ammonias, thereby producing said another salt of said sulfonimide.

* * * * *